(12) United States Patent
Nuzzio

(10) Patent No.: US 7,955,482 B2
(45) Date of Patent: Jun. 7, 2011

(54) WATER-PROOF ELECTROCHEMICAL SENSOR

(75) Inventor: Donald B. Nuzzio, Ringoes, NJ (US)

(73) Assignee: Analytical Systems, Inc., Ringoes, NJ (US)

( * ) Notice: Subject to any disclaimer, the term of this patent is extended or adjusted under 35 U.S.C. 154(b) by 385 days.

(21) Appl. No.: 11/921,049

(22) PCT Filed: May 24, 2006

(86) PCT No.: PCT/US2006/020280
§ 371 (c)(1),
(2), (4) Date: Dec. 11, 2008

(87) PCT Pub. No.: WO2006/127917
PCT Pub. Date: Nov. 30, 2006

(65) Prior Publication Data
US 2009/0127111 A1 May 21, 2009

Related U.S. Application Data

(60) Provisional application No. 60/683,858, filed on May 24, 2005.

(51) Int. Cl.
*G01N 27/28* (2006.01)
*G01N 27/403* (2006.01)

(52) U.S. Cl. .......... 204/400; 204/416; 324/450
(58) Field of Classification Search .......... 204/416–418, 204/435, 400; 324/450
See application file for complete search history.

(56) References Cited

U.S. PATENT DOCUMENTS 3,476,671 A * 11/1969 Petty .............................. 204/400
5,380,422 A * 1/1995 Negishi et al. ........... 204/403.04
5,770,039 A * 6/1998 Rigney et al. ................. 205/789

\* cited by examiner

*Primary Examiner* — Alex Noguerola
(74) *Attorney, Agent, or Firm* — Rohm & Monsanto, PLC

(57) ABSTRACT

A water-proof electrochemical sensor for in situ analysis and real-time monitoring of chemical and biological compounds in a liquid analyte, such as a water column, or a water column/ sediment interface, or sediment. The water-proof electrochemical sensor assembly comprises an electrode body that is resistant to high temperatures and pressure and includes a semi-hard o-ring or collar. A resilient elastomeric boot, that has an internal groove which is adapted to form a tight pressure-fit with the collar is installable on the electrode body. One end of the boot has an opening adapted to form an interference fit with a pin contact for electrical connections with external equipment and the other end of the boot has an opening adapted to form an interference fit with the electrode body whereby a water-proof seal is formed.

7 Claims, 5 Drawing Sheets

WATER-PROOF ELECTROCHEMICAL SENSOR

RELATIONSHIP TO OTHER APPLICATION

This application is a US national stage filing under 35 U.S.C. §371 of International Application No. PCT/US2006/020280 filed on May 24, 2006 and claims the benefit under 35 U.S.C. §119(e) of U.S. Provisional Patent Application Ser. No. 60/683,858, filed May 24, 2005, the disclosure of which is incorporated herein by reference.

Replace third full paragraph, page 7, between lines 20 and 25, with the following paragraph:

As previously noted, there is provided in certain embodiments of the invention an electrical contact 25 that communicates electrically with pin contact 14, and from which extends a wire 27. In such an embodiment, elastomeric boot member 16a is configured to extend upwardly to enclose pin contact 14 and the electrical contact. The extended boot member 16a would form a tight interference fit with the electrical contact or the wire.

BACKGROUND OF THE INVENTION

1. Field of the Invention

This invention relates generally to electrochemical sensors particularly suitable for analysis of multiple chemical species in water columns and sediments, and more particularly, to a water-proof electrochemical sensor.

2. Description of the Related Art

At the surface of our planet, almost all life relies on photosynthesis—the process of using sunlight for energy to create biochemical building blocks—in one way or another. But there are places on earth that never receive sunlight, and yet life flourishes there too. Organisms that live near hydrothermal vents at depths of more than 2500 m rely not on photosynthesis, but on a totally different process called chemosynthesis. Instead of sunlight, these life forms, known as extremophiles, use the energy released from the oxidation of inorganic compounds to build biological molecules necessary for life. Chemicals such as methane, carbon dioxide, sulfur species (such as hydrogen sulfide), iron, manganese, and other trace elements affect the balance of life in this unique ecosystem.

Life has evolved at these volcanically active sites, and it is the center of great interest from biological and biotechnological points of view. Enzymes known as biocatalysts that have been isolated from hydrothermal vent bacteria can be used in the pharmaceutical and biotechnology areas instead of costly synthesized catalysts, which may be less efficient than the true biocatalysts.

The vent sites are also thought to be major contributors of inorganic elements to our oceans. Near these hot vent sites are cooler areas where diffuse vent fluids flow and in which metal sulfides accumulate to form chimney-like structures that can reach tens of meters in height. At these sites, hot hydrothermal vent fluids, 180-400+° C., are being eluted and mixed into the colder seawater, 2-4° C.

However, analyzing the environment of these vents has been a complicated challenge. In most attempts to understand the chemistry of these areas, water samples have been first collected remotely and brought to the surface for instrumental analysis. This process had been the standard for many years. The method of sample collection and the volumes of samples required depended on the types of analyses that would be used, such as atomic absorption, laser-assisted inductively coupled plasma-mass spectroscopy, and ion chemistry. Large water samples are taken from nonmetallic water sampling bottles that can be opened and closed remotely and can hold up to 2 L of water. Samples for gas analysis are taken in gas-tight syringes and sent back to the lab on land for analysis. Smaller sample collection devices are available for other types of analyses.

Although these techniques have aided the understanding of hydrothermal vents, the reduced pressure at the surface can cause outgassing of the samples, which can change their chemistry. There is, therefore, a need for an in situ analyzer that can perform analyses on samples in their respective environments to allow for a truer representation of their complex chemistry.

It is well-known to measure the concentration of various chemical and biological compounds in solution by electrochemical techniques based on oxidation-reduction processes. These techniques employ electrochemical sensors, in the nature of electrode probes. Typical electrode probes comprise gold, platinum, or carbon, and very often are combined with mercury to improve surface reproducibility.

In addition to the foregoing, iridium-based mercury electrodes, are advantageous. Examples of known iridium or mercury/iridium electrodes are found in Buffle, *J. Electroanal. Chem.*, Vol. 216, pages 53-69 (1987); Vitre, et al., *Anal. Chem. Acta*, Vol. 249, pages 419-425 (1991); and U.S. Pat. No. 5,378,343. U.S. Pat. No. 5,578,178 describes a mercury drop electrode. Typical electrochemical sensors, however, are not constructed in a manner that withstands in situ use in a water column or sediment, and particularly use under sea at high temperatures and pressures.

Analytical Instrument Systems, Inc. has produced an electrochemical analyzer that allows for the real-time analysis of the above-described hydrothermal vent areas and offers a tool for the researcher to map out the centers of underwater chemical production. Using this system, a researcher can analyze, in real-time, chemical species such as oxygen, sulfide, iron sulfide, iron, and manganese. The instrument can perform all the standard types of voltammetries: sampled DC, linear sweep, cyclic, normal pulse, differential pulse, squarewave, and all the stripping analyses. The instrument can be controlled via laptop computer from shipboard or submarine, or within a research deep-submergence vehicle (DSV), such as the DSV Alvin operated out of Woods Hole (MA) Oceanographic Institution from which researchers can conduct experiments and collect samples from the floor of the ocean down to 4500 m. Due to the extreme temperature and pressure at which this probe assembly is required to operate, there is a need for an improved water-tight and heat-resistant electrochemical sensor.

It is, therefore, an object of this invention to provide a water-proof electrochemical sensor for in situ analysis of a liquid analyte.

It is another object of this invention to provide a water-proof electrochemical sensor for in situ analysis of a liquid analyte that is particularly useful a high temperatures and pressures.

SUMMARY OF THE INVENTION

The foregoing and other objects are achieved by this invention which provides a water-proof electrochemical sensor assembly for in situ analysis of a liquid analyte, particularly adapted for monitoring chemical or biological compounds in solution, such as in a water column, at a water column/sediment interface, or in sediment.

The electrochemical sensor assembly includes an electrode body for contacting the analyte. The electrochemical sensor assembly includes an electrode body which may be a generally cylindrical elongated housing having an upper contact end and lower sensing end. The housing may comprise ceramic, glass, or plastic, as is known in the art. The housing has an external ridge or protrusion that forms a collar in the vicinity of the upper contact end of the electrode body. In a preferred embodiment, the collar is a semi-hard o-ring that fits tightly around the electrode body. In an alternative embodiment, the collar is formed integrally with electrode body.

The electrochemical sensor, or sensors, are housed within the electrode body and may comprise working, reference, and counter electrodes as is known in the art. In a practical embodiment, the electrochemical sensor(s) extend from, or are at least contiguous with, a lower sensing end of the electrode body. In a practical embodiment, the sensor is potted in a polymer to form a water-tight seal at the sensing end of the electrode body so that only the sensor tip, which in one embodiment may be an electrode wire, contacts the analyte.

While the electrode body shown herein is generally cylindrical, in certain embodiments, particularly those embodiments adapted to be deployed in sediment, the sensing end of the electrode body may be conical in shape.

The electrochemical sensor(s) are electrically coupled to a contact for electrically connecting the electrochemical sensor(s) housed within the electrode body to external electronics. The contact may comprise a pin contact extending from the upper end of the electrode body distal to the lower sensing end. In order to protect the electrical connections, a resilient elastomeric, generally cylindrical boot is provided to form a water-tight seal at the upper end of the electrode body. The elastomeric boot has an upper end and a lower end and an internal groove adapted to form a tight pressure-fit with the collar on the electrode body. The upper end of the boot has an opening which is slightly smaller in diameter than the pin contact so that it forms a tight interference fit with the pin contact. The lower end of the boot has an opening that has a diameter that is slightly smaller than the diameter of the electrode body so that is forms a tight interference fit with the electrode body. In this manner, the elastomeric boot forms a water-proof seal around the upper contact end of the electrode body.

BRIEF DESCRIPTION OF THE DRAWING

Comprehension of the invention is facilitated by reading the following detailed description, in conjunction with the annexed drawing, in which.

DETAILED DESCRIPTION

Figure 1:
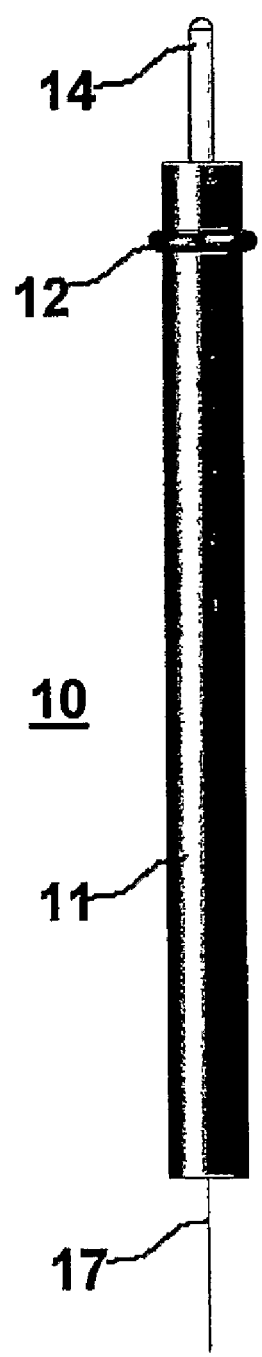
FIG. 1 is a side plan view of an electrode body constructed in accordance with the present invention.

FIG. 1 is a side plan view of water-proof electrochemical sensor assembly 10 comprising an elongated, generally cylindrical polymeric electrode body 11. A semi-hard o-ring comprises a collar 12 and forms a water-proof seal between a rubber boot 16 (not shown in this figure) and the electrode body. Of course, collar 12 can be formed integrally with electrode body 11. As will be shown in FIG. 4, a plurality of collars, such as collars 12a, 12b, and 12c, are arranged axially on electrode body 11 to enhance overall water tightness. As shown in the drawing, a pin contact 14 extends from the upper end of the electrode body. Pin contact 14 electrically connects the sensor(s) that are housed internally within electrode body 11 to the desired electronics.

The body of the electrode (not shown in this figure) is a ceramic, glass, or plastic, as is known in the art. In an advantageous embodiment, the body is a hard, durable water-resistant epoxy or modified polymer, illustratively a thermoplastic, such as polyether ether ketone (PEEK). O-ring 12 comprises a semi-hard polymer, illustratively the same polymer as the body of the electrode. In another preferred embodiment, the electrode body is a ceramic material that can withstand high pressure and elevated temperatures, such as that found in a hydrothermal vent in the ocean floor.

Illustratively, the sensor of this particular embodiment comprises a sensor wire 17 that extends from the lower end of the electrode body distal to the contact end from which pin contact 14 extends. Sensor wire 17 may comprise any known metal or combination of metals, such as gold, platinum, gold/mercury, iridium, iridium/mercury, etc. While the sensor is shown here as a wire, it is to be understood that the sensor may be in any known form, such as an individual sensor or an array of sensors, formed by any technique such as screen-printing, lithography, or various deposition techniques. Preferably, both potentiometric and voltammetric sensors are provided.

Figure 2:
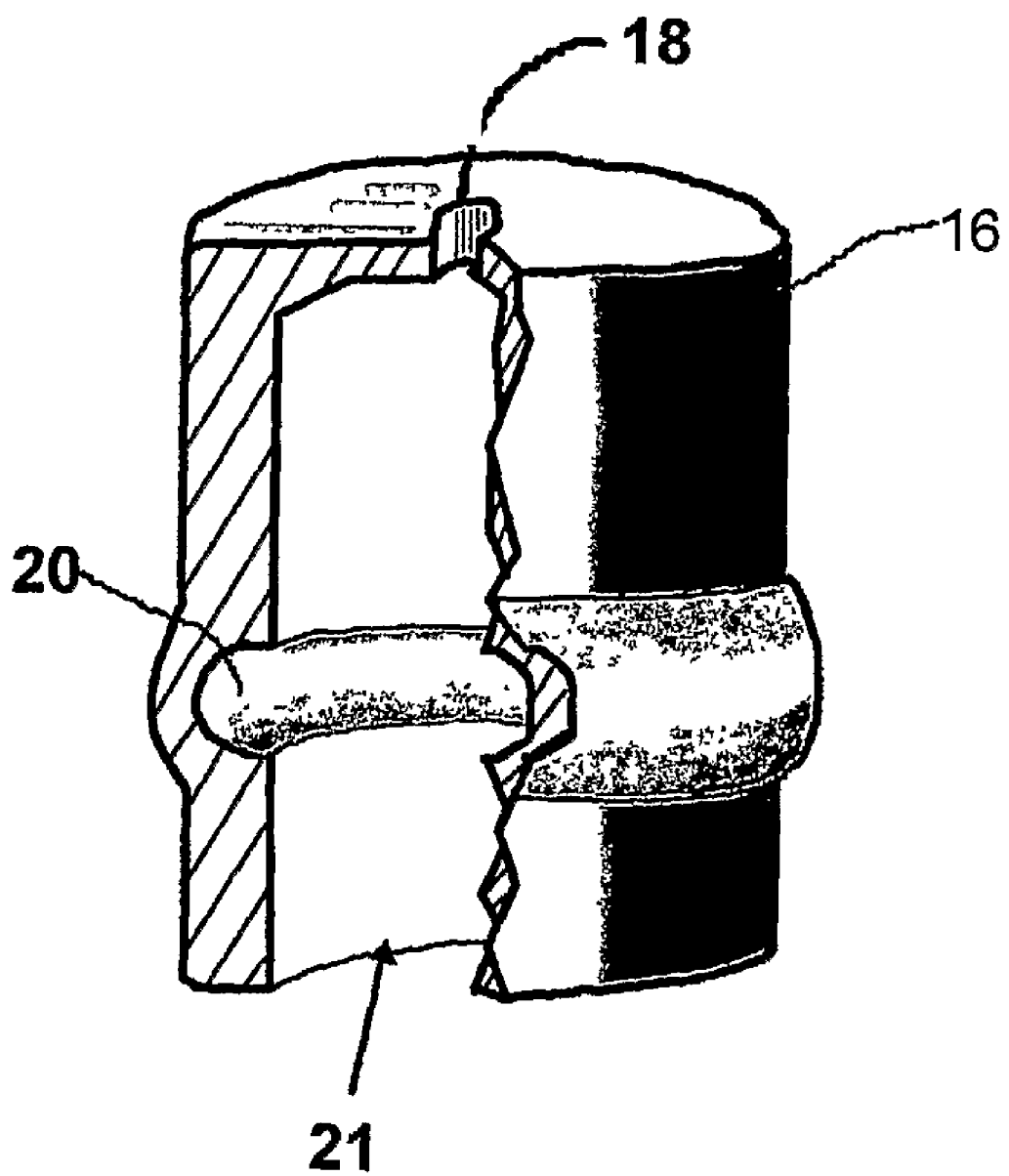
FIG. 2 is a partially fragmented and cross-sectional representation of an elastomeric boot member constructed in accordance with the principles of the invention.

FIG. 2 is a partially fragmented and cross-sectional representation of a resilient elastomeric boot member 16 constructed in accordance with the principles of the invention. The boot member 16, is illustratively fabricated of a resilient material, such as rubber, or silicone, which will remain resilient under the conditions expected to be encountered in the analyte, such as sea water, under high pressure and/or temperature. There is an internal groove 20 that is formed within the interior of boot 16. Collar 12 (see FIG. 1) fits within groove 20 to form a tight pressure-fit seal. The upper end of boot 16 has an opening 18 which is slightly smaller in diameter than the pin contact (see, pin 14 in FIG. 1) so that it forms a tight interference fit with the pin contact. The lower end of the boot has an opening 21 that, in preferred embodiments, has a diameter that is slightly smaller than the diameter of the electrode body so that is forms a tight interference fit with the electrode body. In this manner, elastomeric boot 16 forms a water-proof seal around the upper contact end of the electrode body as shown in FIG. 3.

Figure 3:
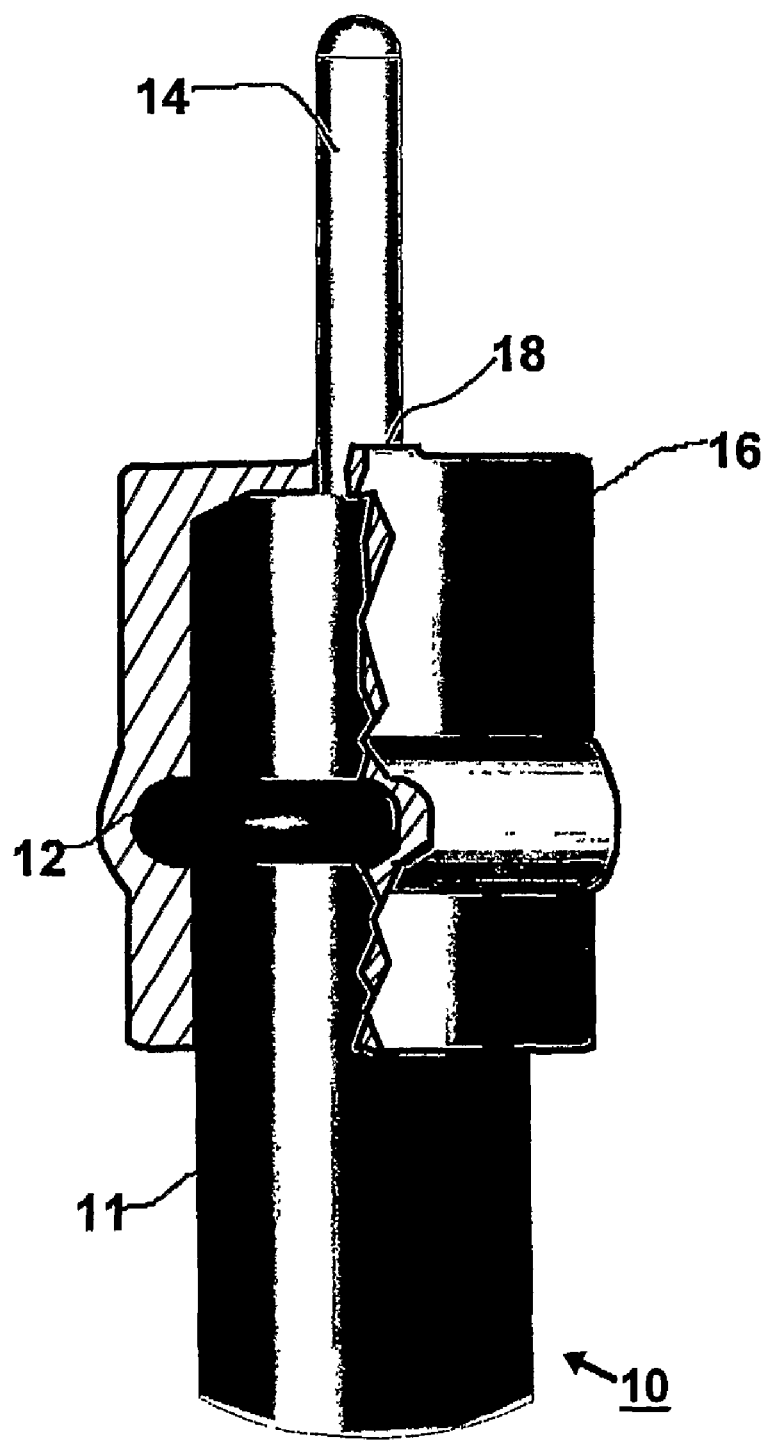
FIG. 3 is a fragmented and cross-sectional isometric representation of the elastomeric boot member of FIG. 2 installed on the electrode body of FIG. 1.

FIG. 3 is a fragmented and cross-sectional isometric representation of the elastomeric boot member 16 of FIG. 2 installed on the electrode body 11 of FIG. 1. Elements that are the same as in FIGS. 1 and 2 bear the same reference numerals. Collar 12 of electrode body 11 is shown pressure-fit within groove 12 in boot 16. Pin contact 14 is shown extending through opening 18 to form a tight interference fit with boot 16. The result is a water-proof in situ electrochemical sensor assembly 10 in accordance with the present invention. In some embodiments, however, there is provided an electrical contact (not shown) that communicates electrically with pin contact 14, and from which extends a wire (not shown). In such an embodiment, elastomeric boot member 16 is configured to extend upwardly to enclose both, pin contact 14 and the electrical contact, and in some embodiments, a portion of the wire. The extended boot member 16 would form a tight interference fit with the electrical contact or the wire.

Figure 4:
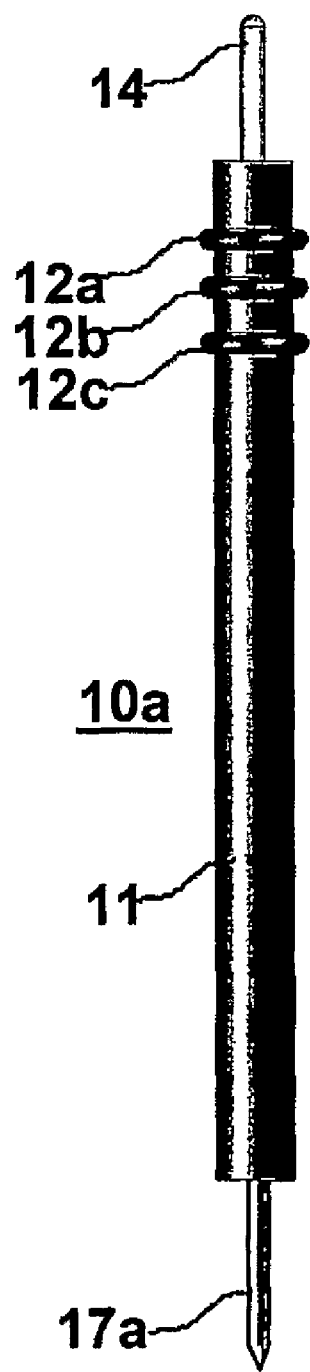
FIG. 4 is a side plan view of an electrode body constructed in accordance with the present invention and shows multiple sealing collars axially arranged.

FIG. 4 is a side plan view of an electrode body 10*a* constructed in accordance with the present invention and shows multiple sealing collars 12*a*, 12*b*, and 12*c* axially arranged. Elements of structure that have previously been discussed are similarly designated. This figure additionally shows a sensor element 17*a* that is not in needle form, as shown hereinabove in relation to FIG. 1, which needle is particularly useful for penetrating the sea floor sediment with minimum disturbance. Instead, sensor element 17*a* may have a significantly larger diameter, illustratively between 0.125" and 0.25".

Figure 5:
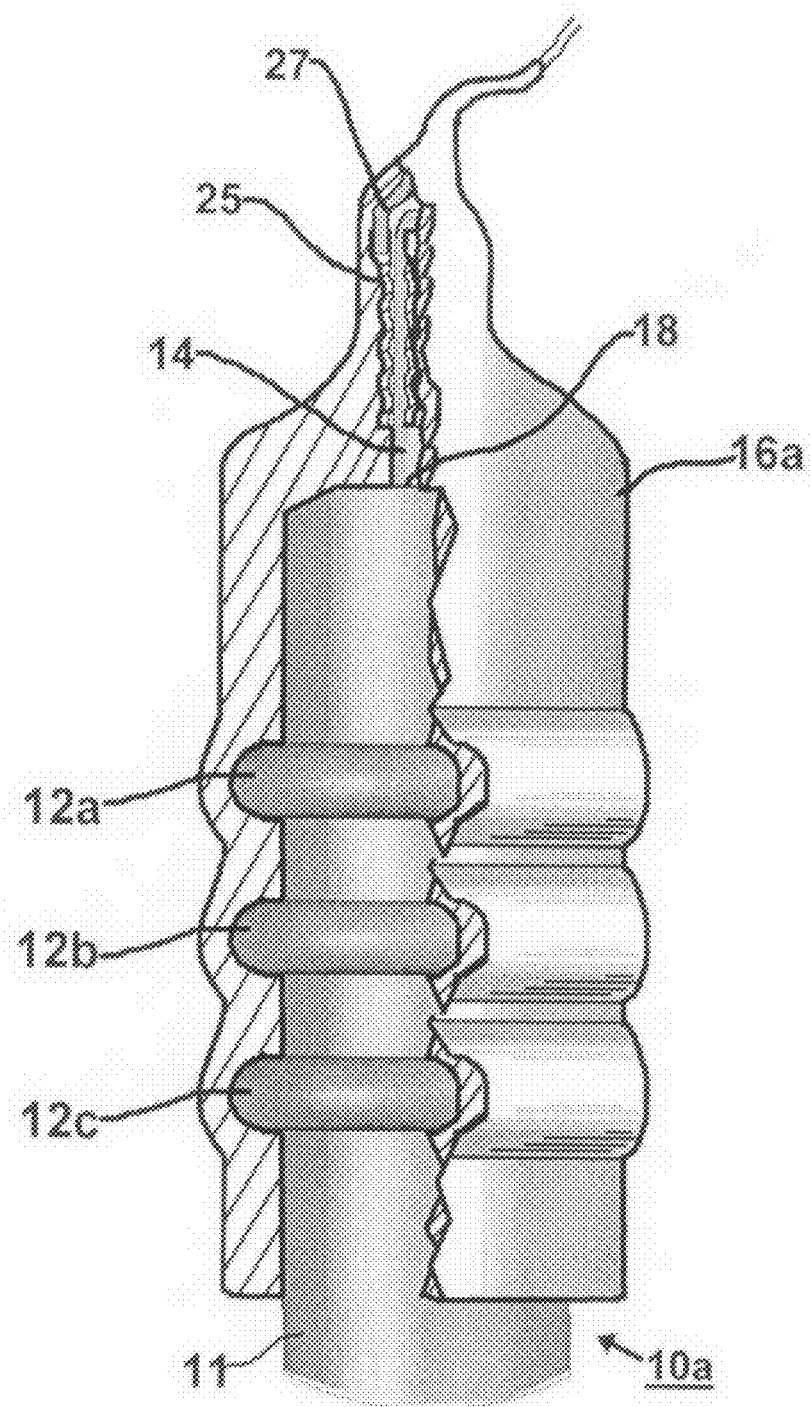
FIG. 5 is a fragmented and cross-sectional isometric representation of an elastomeric boot member installed on the electrode body of FIG. 4.

FIG. 5 is a fragmented and cross-sectional isometric representation of an elastomeric boot member 16*a* installed on electrode body 10*a* of FIG. 4. Elements of structure that have previously been discussed are similarly designated. As shown in this figure, elastomeric boot member 16*a* is configured to accommodate therewithin the three sealing collars 12*a*, 12*b*, and 12*c* that are shown axially arranged in relation to one another on electrode body 10*a*. This arrangement increases the ability of the overall structure to remain waterproof at extended depths under the sea.

As previously noted, there is provided in certain embodiments of the invention an electrical contact (not shown) that communicates electrically with pin contact 14, and from which extends a wire (not shown). In such an embodiment, elastomeric boot member 16*a* is configured to extend upwardly to enclose pin contact 14 and the electrical contact. The extended boot member 16*a* would form a tight interference fit with the electrical contact or the wire.

Although the invention has been described in terms of specific embodiments and applications, persons skilled in the art may, in light of this teaching, generate additional embodiments without exceeding the scope or departing from the spirit of the invention claimed herein. Accordingly, it is to be understood that the drawing and description in this disclosure are proffered to facilitate comprehension of the invention, and should not be construed to limit the scope thereof.

What is claimed is:

1. A water-proof electrochemical sensor for in situ analysis of a liquid analyte comprising:

an electrode body for contacting the analyte having an upper contact end and lower sensing end, electrode body having an electrode body surface at the upper contact end;

a collar attached to the electrode body surface of said electrode body axially inward of the upper contact end;

at least one electrochemical sensor contained within said electrode body and extending from the lower sensing end for contacting the analyte;

a pin contact for electrically connecting said at least one electrochemical sensor to external electronics extending from the upper contact end; and a resilient elastomeric generally cylindrical boot having an upper end and a lower end and an internal groove adapted to press-fit the collar, the upper end of the boot having an opening adapted to form a tight interference fit with said pin contact and the lower end of the boot having an opening adapted to form tight interference fit with the electrode body whereby a water-proof seal is formed around the upper contact end of the electrode body for undersea depths.

2. The water-proof electrochemical sensor of claim 1, wherein said at least one electrochemical sensor comprises a wire needle.

3. The water-proof electrochemical sensor of claim 1, wherein said at least one electrochemical sensor comprises a sensor element having a diameter of approximately 0.125".

4. The water-proof electrochemical sensor of claim 1, wherein said at least one electrochemical sensor comprises a sensor element having a diameter of approximately 0.25".

5. The water-proof electrochemical sensor of claim 1, wherein there is provided a further collar attached further axially inward to said electrode body.

6. The water-proof electrochemical sensor of claim 5, wherein said resilient elastomeric generally cylindrical boot is arranged to overlie said collar and said further collar.

7. The water-proof electrochemical sensor of claim 1, wherein said resilient elastomeric generally cylindrical boot is configured to enclose said pin contact.

* * * * *